US008684431B2

(12) United States Patent
Setozaki et al.

(10) Patent No.: US 8,684,431 B2
(45) Date of Patent: Apr. 1, 2014

(54) DUPLEX-TYPE PRODUCT BAG UNLOADING APPARATUS

(75) Inventors: Masakazu Setozaki, Iwakuni (JP); Yasuyuki Honda, Iwakuni (JP)

(73) Assignee: Toyo Jidoki Co., Ltd., Tokyo (JP)

( * ) Notice: Subject to any disclaimer, the term of this patent is extended or adjusted under 35 U.S.C. 154(b) by 377 days.

(21) Appl. No.: 13/171,213

(22) Filed: Jun. 28, 2011

(65) Prior Publication Data
US 2011/0318147 A1 Dec. 29, 2011

(30) Foreign Application Priority Data

Jun. 29, 2010 (JP) ................................. 2010-148099

(51) Int. Cl.
*B66C 1/28* (2006.01)
*B65G 29/00* (2006.01)

(52) U.S. Cl.
USPC ...................... 294/87.22; 198/465.4; 198/680

(58) Field of Classification Search
USPC .............. 198/465.4, 468.1, 680, 683; 53/302, 53/459; 414/917; 294/28, 87.1, 87.22, 214
See application file for complete search history.

(56) References Cited

U.S. PATENT DOCUMENTS

| | | | | | |
|---|---|---|---|---|---|
| 4,473,989 | A | * | 10/1984 | Tsutsumi et al. | ................ 53/459 |
| 4,505,636 | A | * | 3/1985 | Sugino et al. | ................. 414/736 |
| 5,487,700 | A | * | 1/1996 | Dillard | ........................... 452/188 |
| 5,782,685 | A | * | 7/1998 | Hazenbroek et al. | ......... 452/138 |
| 5,862,653 | A | * | 1/1999 | Solano | ............................. 53/562 |
| 5,967,739 | A | * | 10/1999 | Bennison | .................... 414/744.3 |
| 6,474,049 | B1 | * | 11/2002 | Lipes et al. | ...................... 53/494 |
| 6,644,462 | B2 | * | 11/2003 | Hiramoto et al. | ........... 198/478.1 |
| 6,712,196 | B2 | * | 3/2004 | Ikemoto et al. | ............ 198/468.2 |
| 7,021,036 | B2 | * | 4/2006 | Hiramoto et al. | ............... 53/562 |
| 7,232,365 | B2 | * | 6/2007 | Annema et al. | ............... 452/167 |
| 8,360,232 | B2 | * | 1/2013 | Hazenbroek | .................. 198/682 |

FOREIGN PATENT DOCUMENTS

| | | |
|---|---|---|
| JP | S61-33915 A | 2/1986 |
| JP | S63-57297 B | 11/1988 |
| JP | H09-254931 A | 9/1997 |
| JP | 3116531 B | 12/2005 |
| JP | 3984740 B | 10/2007 |

* cited by examiner

*Primary Examiner* — Douglas Hess
(74) *Attorney, Agent, or Firm* — DLA Piper LLP (US)

(57) ABSTRACT

A duplex-type product bag unloading apparatus including two downwardly opening and closing chucks and a chuck-moving mechanism for reciprocating the chucks between positions for receiving and discharging product bags. The relative positions of the two chucks are changed as they are moved from the receiving position to the discharging position by the chuck-moving mechanism, so that in the receiving position, the chucks are arranged in a single row in the bag width direction of the grasped product bags, and in the discharging position, the chucks are in a single row in the thickness direction of the grasped product bags. The chuck-moving mechanism is comprised of a pivot arm and a chuck-supporting frame rotatably mounted to the pivot arm, and the two chucks are rotatably mounted on both sides of the chuck-supporting frame. The chuck-supporting frame and the chucks rotate in synchronism with the pivotal motion of the pivot arm.

12 Claims, 12 Drawing Sheets

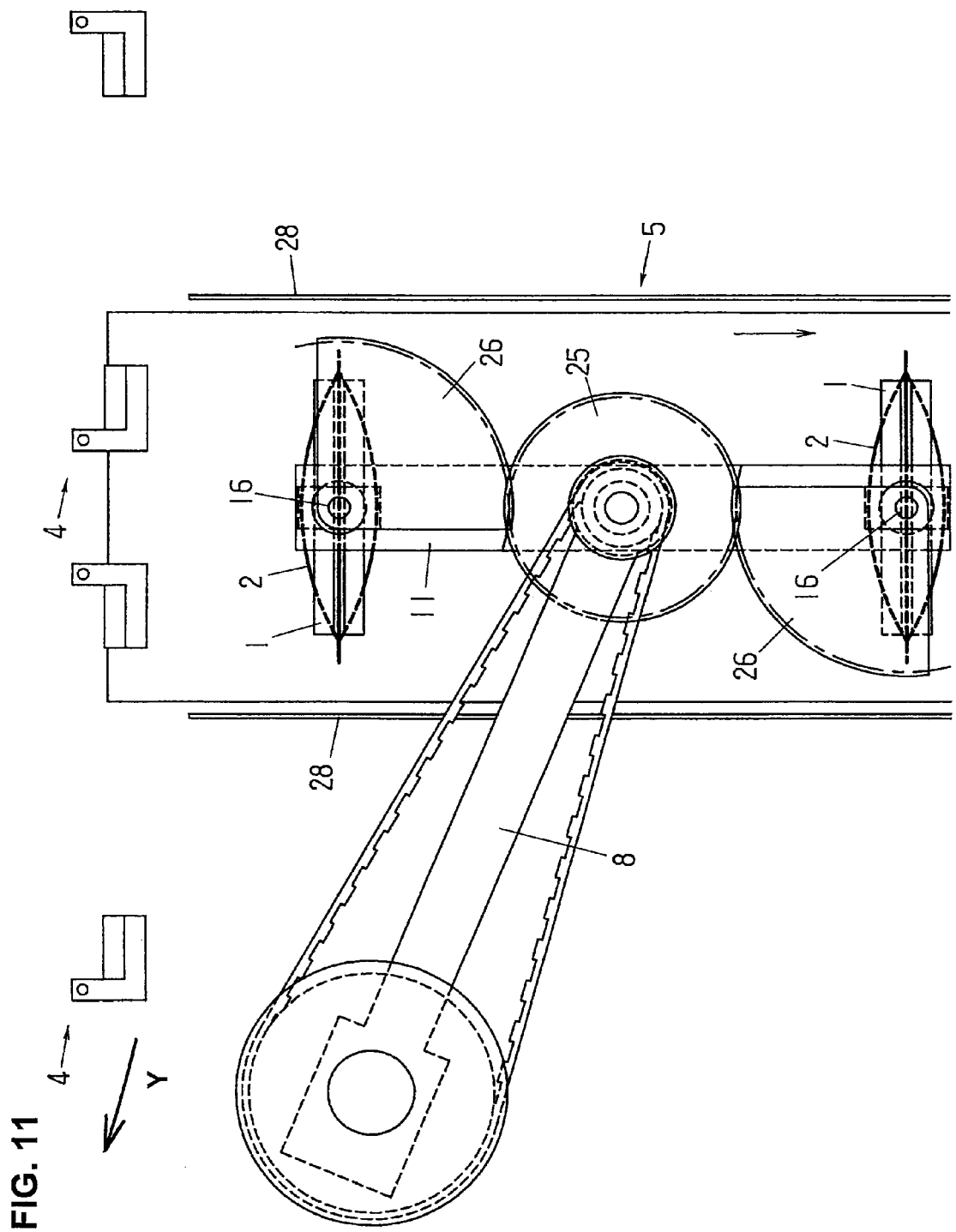

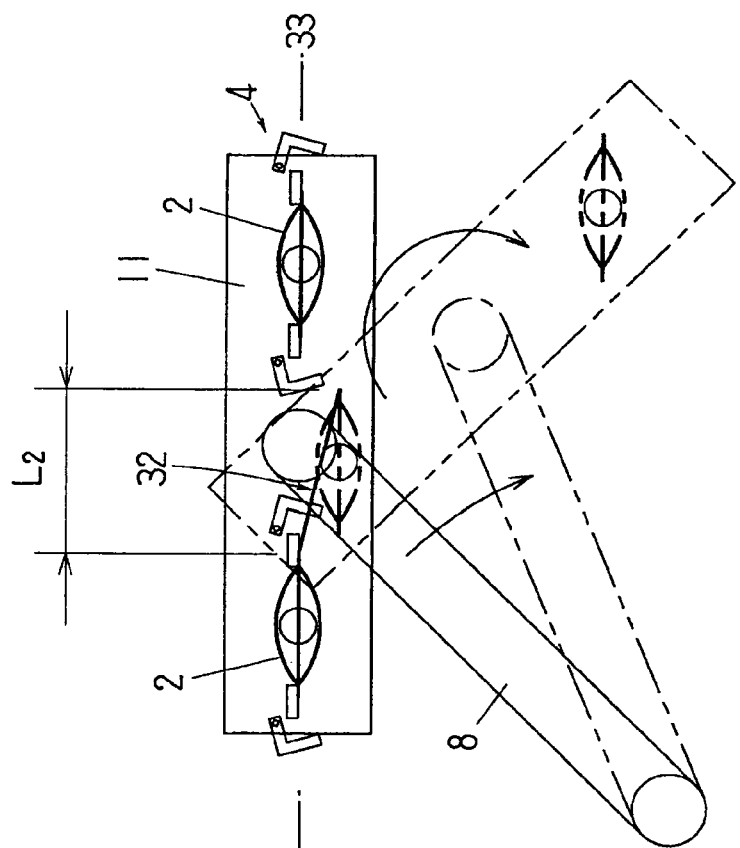
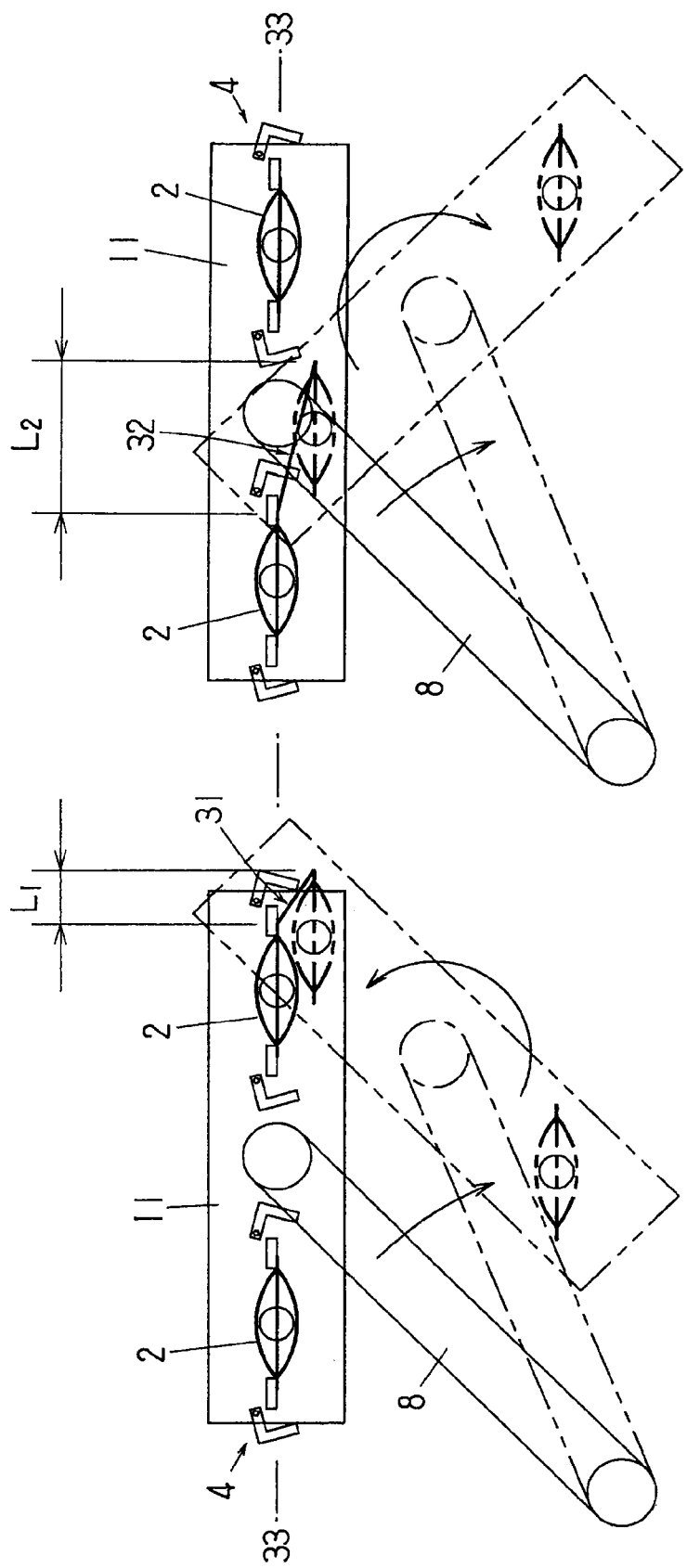
FIG. 12(a)
FIG. 12(b)

DUPLEX-TYPE PRODUCT BAG UNLOADING APPARATUS

BACKGROUND OF THE INVENTION

Field of the Invention

The present invention relates to a duplex-type product bag unloading apparatus used to unload filled and sealed product bags fabricated by a duplex type intermittently-conveying bag packaging machine from this packaging machine.

As shown in Japanese Patent Application Publication (Kokoku) No. S63-57297 and Japanese Utility Model Registration No. 3116531, a duplex type intermittently-conveying bag packaging machine includes two pairs of pairs of grippers that, forming a single group, grip the right and left side upper edges of bags and suspend them mouth-side-up. Multiple groups of pairs of grippers are installed at a constant pitch along a predetermined travel path, so that the gripping surfaces of the two pairs of pairs of grippers belonging to the same group are, when gripping the respective bags, disposed in substantially the same plane. As each group of pairs of grippers intermittently travels along the travel path, each one of the two pairs of pairs of grippers belonging to the same group is simultaneously supplied with a single bag (with a total of two bags). In the course of the subsequent packaging operations, each one of the bags gripped by the two pairs of pairs of grippers belonging to the same group is simultaneously subjected to successive packaging operations, such as opening of the mouth of the bag, filling of the bag with material to be packaged, sealing of the mouth of the bag, etc. While the travel path of the pairs of grippers disclosed in Japanese Patent Application Publication (Kokoku) No. S63-57297 and Japanese Utility Model Registration No. 3116531 is circular, the travel path may also be linear or racetrack-shaped.

The advantage of duplex type intermittently-conveying bag packaging machines in comparison with simplex-type intermittently-conveying bag packaging machines is their superior productivity (see Japanese Patent Application Laid-Open (Kokai) Nos. S61-33915 and H9-254931 and Japanese Patent No. 3984740, for instance) due to their ability to process two bags simultaneously.

Typically, when two product bags fabricated by a duplex type intermittently-conveying bag packaging machine are simultaneously discharged (released by the pairs of grippers) from the bag packaging machine, the bags are dropped onto a carry-out conveyor without further additional arrangement and taken out of the packaging machine in a double-row arrangement by the carry-out conveyor (see Japanese Utility Model Registration No. 3116531).

On the other hand, subsequent treatment operations (sterilization, case packing, etc.) may sometimes require that the carry-out conveyor carry the bags out in a single row. For example, in Japanese Patent Application Publication (Kokoku) No. S63-57297, an intermediate conveyor, which is substantially perpendicular to the carry-out conveyor, is disposed between the carry-out conveyor and the bag packaging machine; and by way of transferring the product bags from the intermediate conveyor to the carry-out conveyor, the configuration to transport the product bags is converted from double-row transportation (which is on the intermediate conveyor) to single-row transportation (which is on the carry-out conveyor).

When the intermediate conveyor is disposed as described in Japanese Patent Application Publication (Kokoku) No. S63-57297, the orientation of the transported product bags is switched from the bag length or height direction (longitudinal direction) on the intermediate conveyor to the bag width direction on the carry-out conveyor. Accordingly, the method of this Japanese Patent Application Publication (Kokoku) No. S63-57297 is not applicable when the orientation of the product bags conveyed in a single row needs to be in the length direction of the bags. Another problem is that transferring (dropping) of bags from the intermediate conveyor onto the carry-out conveyor shifts the orientation and positions of the product bags and disturbs their alignment caused by the vertical drop from the intermediate conveyor onto the carry-out conveyor.

BRIEF SUMMARY OF THE INVENTION

The present invention is to solve the problems described above that arise when pairs of product bags are simultaneously removed from a duplex type intermittently-conveying bag packaging machine, and it is an object of the present invention to provide a duplex-type product bag unloading apparatus that allows product bags to be released from grippers of a packaging machine and carried out onto a carry-out conveyor in such a manner that the length or height direction of the bags is oriented in the direction of conveyance of the carry-out conveyor and the bags are aligned in a single row.

The above-described object is accomplished by a unique structure of the present invention for a duplex-type product bag unloading apparatus that receives two filled and sealed product bags, which are gripped by separate pairs of grippers respectively on left and right edges thereof, suspended mouth-side-up at equal heights, and arranged in a single row in a width direction thereof at a predetermined distance apart from each other, from the pairs of grippers and discharges the bags onto a carry-out conveyor; and in the present invention, the bag unloading apparatus includes:

- two downwardly opening and closing chucks for grasping, from above, areas around mouths of the product bags gripped by the pairs of grippers, and
- a chuck-moving mechanism for reciprocating the two chucks between a product bag-receiving position and a discharging position which is remote from the receiving position; and
- when the two chucks travel from the receiving position to the discharging position, relative positions thereof of the chucks are changed by the chuck-moving mechanism such that in the receiving position, the chucks are arranged in a single row along a bag width direction of the grasped product bags, and in the discharging position, the chucks are arranged in a single row along a thickness direction of the grasped product bags.

In the above-described duplex-type product bag unloading apparatus of the present invention, when the product bags are grasped by the chucks, the grasping surfaces of the chucks lie within a substantially vertical plane oriented along the width direction of the product bags. Accordingly, as to the arrangement of the two chucks, in the (bag) receiving position, the chucks are arranged in a single row along the direction of the grasping surfaces, and, in the (bag) discharging position, the chucks are arranged in a single row along a direction perpendicular to the grasping surfaces of the chucks.

In this duplex-type product bag unloading apparatus, if the direction of conveyance of the carry-out conveyor is set to the same direction as that of the row of the chucks in the discharging position, the product bags that are released from the chucks and dropped onto the carry-out conveyor are carried out on the carry-out conveyor in a single-row alignment so that the length direction of the bags is oriented on the carry-out conveyer along the direction of conveyance.

In the duplex-type product bag unloading apparatus of the present invention:

(1) The orientation of the width direction of the product bags grasped by the chucks is kept substantially constant while the chucks reciprocate between the receiving position and discharging position. In this case, the individual chucks make a translational motion, and there is no rotation about the centers of gravity of the product bags grasped by the chucks, and the deflection and shifting of the product bags while in motion are reduced.

(2) The chuck-moving mechanism of duplex-type product bag unloading apparatus includes a pivot arm which is coupled to a drive source and pivots back and forth through a predetermined angular range in a horizontal plane, and a chuck-supporting frame, which is journaled on the free end of the pivot arm for making reciprocating rotary motion in the horizontal plane; and wherein the two chucks are rotatably supported in the horizontal plane on opposite sides of a pivot shaft of the chuck-supporting frame, and while the pivot arm pivots back and forth, the chuck-supporting frame rotates back and forth through a predetermined angular range with respect to the pivot arm, and the two chucks rotate back and forth through a 90-degree range with respect to the chuck-supporting frame.

In this structure, while the chuck-supporting frame and/or chucks, as described below, can use the drive source of the pivot arm as the drive source of the rotation, a separate drive source can also be provided therefor.

(3) In the structure (2) described above, the orientation of the width direction of the product bags grasped by the chucks is kept substantially constant while the chucks reciprocate between the receiving position and the discharging position.

(4) In the structures (2) and (3) described above, the reciprocating rotary motion of the chuck-supporting frame and the two chucks is set so as to be in synchronism with the reciprocating pivotal motion of the pivot arm. This improves the processing capability of the product bag unloading apparatus.

(5) In this structure (4), the direction of the reciprocating rotary motion of the chuck-supporting frame is set so as to be oriented in a direction opposite to the direction of rotation of the reciprocating pivotal motion of the pivot arm.

(6) In the above-described structures (4) and (5), the drive source that rotates the chuck-supporting frame and the two chucks back and forth is the same as (or common to) the drive source that pivots the pivot arm back and forth; the chuck-moving mechanism includes a chuck-supporting frame rotation mechanism, which transmits the driving force of the drive source to the chuck-supporting frame; and a chuck rotation mechanism, which further transmits the driving force transmitted by the chuck-supporting frame rotation mechanism to the two chucks. Since the drive source of the rotation of the chuck-supporting frame and chucks is the same as (or commonly used as) the drive source of the pivot arm, the entire structure of the product bag unloading apparatus can be simplified, permitting cost reduction.

(7) In this structure (6), the chuck-supporting frame rotation mechanism includes a first pulley provided at a turning center of the pivot arm, a second pulley provided on the pivot shaft of the chuck-supporting frame, and a belt provided over the first pulley and second pulley; and the chuck rotation mechanism includes a first gear provided at the free end of the pivot arm and coaxial with the pivot shaft of the chuck-supporting frame, a pair of second gears provided on pivot shafts of the two chucks, and a pair of third gears which are rotatably mounted on the chuck-supporting frame in such a manner that the third gears are respectively interposed between the first gear and second gears while being in mesh with the first and second gears.

(8) Furthermore, the chuck-moving mechanism include a pivot arm which is coupled to a drive source and pivots back and forth through a predetermined angular range in a horizontal plane, and a chuck-supporting frame which is attached to the free end of the pivot arm; the two chucks are rotatably supported in the horizontal plane on the chuck-supporting frame; and while the pivot arm pivots back and forth, the two chucks rotate back and forth through a 90-degree range with respect to the chuck-supporting frame. In this structure, though the chuck-moving mechanism can be simplified in comparison with the case that involves reciprocating rotary motion of the chuck-supporting frame, the angle of the reciprocating pivotal motion of the pivot arm needs to increase. In this case as well, the orientation of the width direction of the product bags grasped by the chucks can be kept substantially constant while the chucks reciprocate between the receiving position and discharging position, and the reciprocating rotary motion of the two chucks can be set so as to be in synchronism with the reciprocating pivotal motion of the pivot arm.

(9) The above-described duplex-type product bag unloading apparatus of the present invention is used for the transfer of product bags made by, for instance, a duplex type intermittently-conveying bag packaging machine. In such a duplex type intermittently-conveying bag packaging machine, two pairs of pairs of grippers for griping right and left side edges of bags and suspending the bags mouth-side-up constitute a single group, multiple groups of the pairs of grippers are installed at a constant pitch along a circular travel path, gripping surfaces of the two pairs of the pairs of grippers belonging to a same group are disposed in substantially the same plane when gripping respective bags; and as each group of the pairs of grippers intermittently travels along the travel path, each one of the two pairs of the pairs of grippers belonging to the same group is simultaneously furnished with a single bag and, in a course of subsequent packaging operations, the bags gripped by the two pairs of pairs of grippers belonging to the same group are subjected to successive simultaneous packaging operations including opening mouth of bag, filling bag with material to be packaged, and sealing the mouth of the bag.

As seen from the above, the duplex-type product bag unloading apparatus according to the present invention is capable of simultaneously receiving two product bags made by a duplex type intermittently-conveying bag packaging machine, etc. and released from grippers thereof, and the unloading apparatus further orients the length direction of the two product bags in the direction of conveyance of a carry-out conveyor and transfers them onto the carry-out conveyor in a single-row alignment.

BRIEF DESCRIPTION OF THE SEVERAL VIEWS OF THE DRAWINGS

FIG. 11 is a plan view of the other duplex-type product bag unloading apparatus with the chucks in the discharging position; and FIGS. 12(a) and 12(b) are explanatory illustrations showing the interference relationship between the grippers, the bags, and the direction of rotation of the chuck-supporting frame.

DETAILED DESCRIPTION OF THE INVENTION

The duplex-type product bag unloading apparatus according to the present invention will be described below in detail with reference to FIGS. 1 through 12(b).

First Embodiment

The first embodiment of the duplex-type product bag unloading apparatus of the present invention is shown in FIGS. 1 through 6 and will be described below first.

Figure 1:
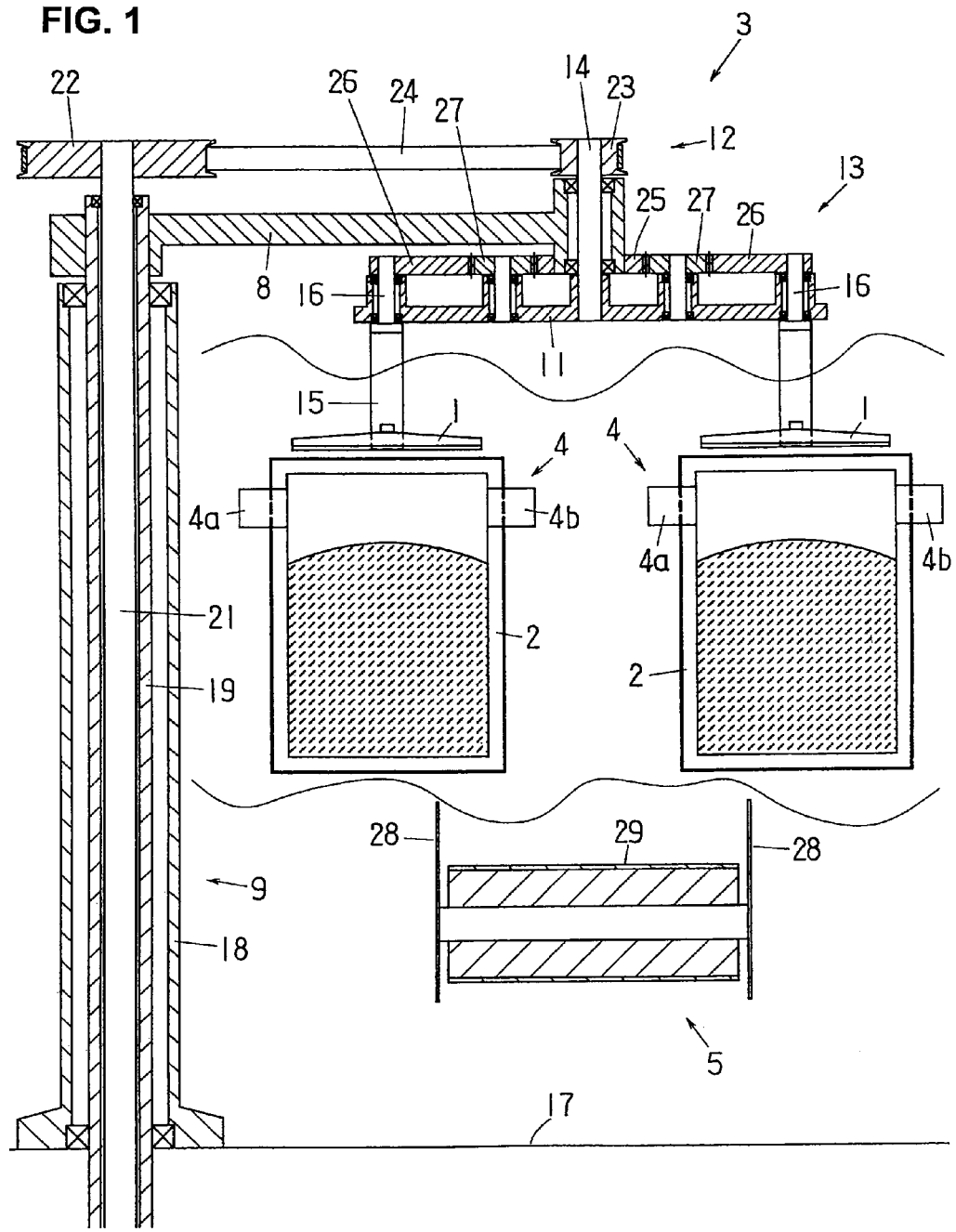
FIG. 1 is a partial cross-sectional front view of a duplex-type product bag unloading apparatus according to the present invention with the chucks in the receiving position (with the chucks open)
Figure 2:
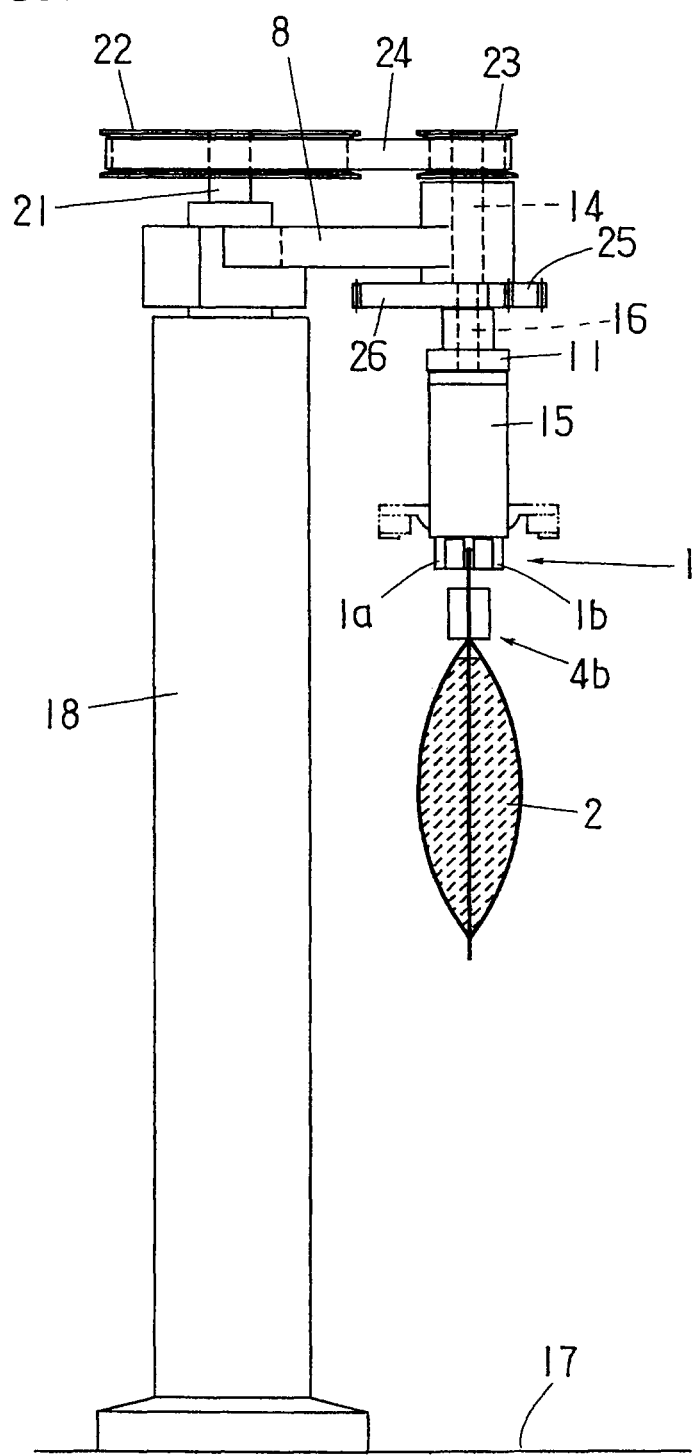
FIG. 2 is a side view thereof (with the chucks closed)
Figure 3:
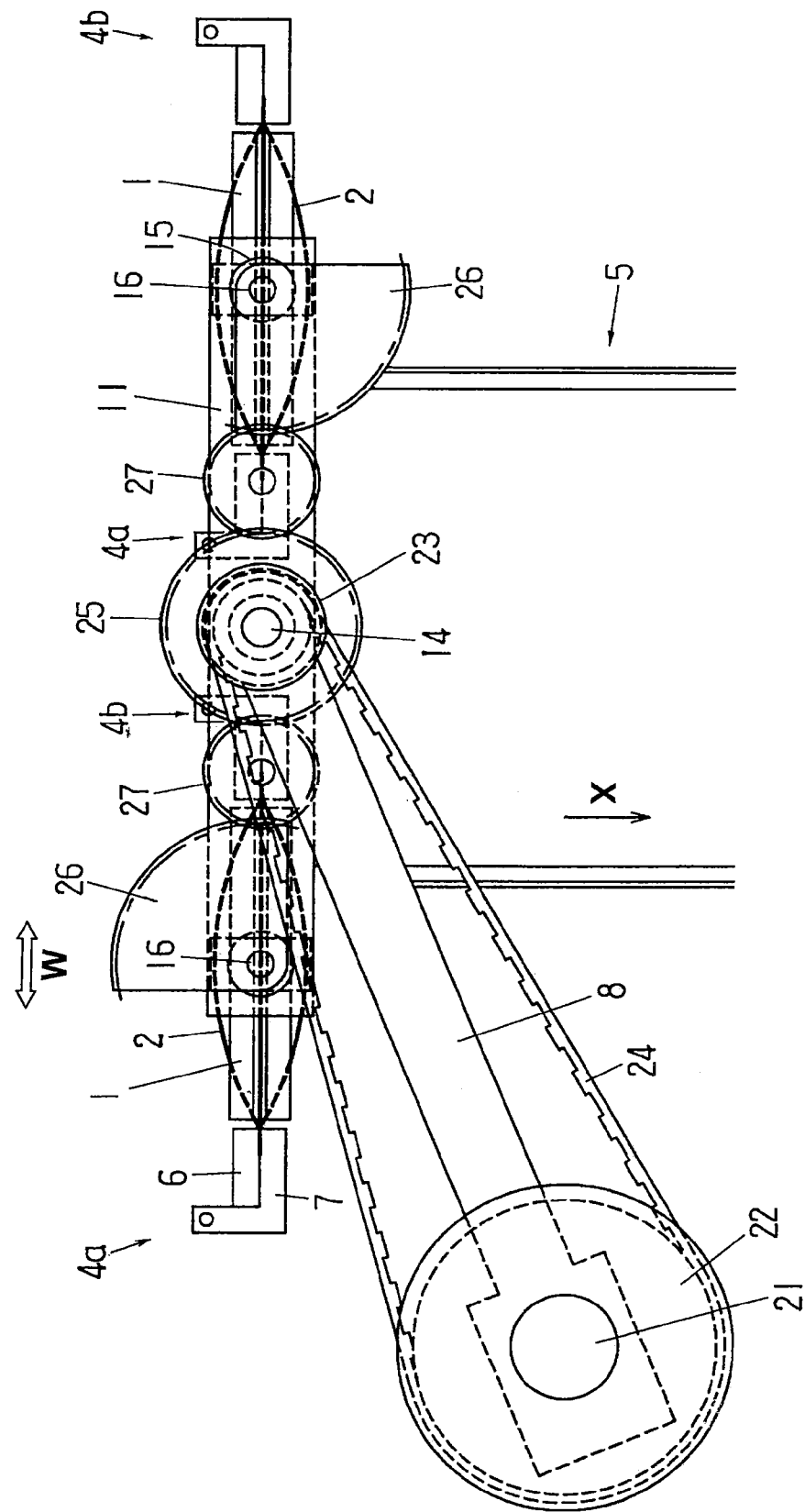
FIG. 3 is a plan view thereof (with the chucks closed)

As seen from FIGS. 1 through 3, the duplex-type product bag unloading apparatus of the present invention includes chucks 1 and a chuck-moving mechanism 3 that moves the chucks 1 between a receiving position used for receiving product bags 2 and a discharging position remote from the receiving position, and this bag unloading apparatus receives product bags 2 from two pairs of grippers 4 of a duplex type intermittently-conveying bag packaging machine (only the pairs of grippers 4 are shown) and discharges them onto a carry-out conveyor 5. In the shown structure, the intermittently traveling pairs of grippers 4 of the bag packaging machine have a circular travel path, and the duplex-type product bag unloading apparatus is disposed on the outside of the travel path, with the direction of conveyance of the carry-out conveyor 5, as depicted by the arrows X in FIGS. 3 and 5, being set substantially perpendicular to the direction of travel (indicated by the arrow Y in FIG. 5) of the pairs of grippers 4 (in the radial direction with respect to the travel path of the pairs of grippers 4).

In an intermittently-conveying bag packaging machine, the pairs of grippers 4 are those elements generally used for gripping, typically, the right and left upper edges of product bags 2 at locations slightly below the mouth and intermittently rotating them, with every two pairs constituting a single group. The right and left grippers 4a and 4b, which form pairs of grippers 4, take a symmetrical structure and include a fixed gripping member 6 on the inside and a movable gripping member 7 on the outside, respectively (see FIG. 3). The movable gripping member 7, which has a hooked shape in plan view, pivots to open and close in the horizontal plane outwardly and inwardly with respect to the outside of the fixed gripping member 6. When it is closed inwardly, the product bag 2 is gripped between movable and fixed gripping members 6 and 7; and when it is opened outwardly, the product bag 2 is released therefrom. When a bag is gripped, all the gripping surfaces of the right and left grippers 4a and 4b of the two pairs of pairs of grippers 4 belonging to the same group (fixed gripping member 6 and movable gripping member 7) are disposed such that they are in the same substantially vertical plane. Consequently, the product bags 2 gripped by the pairs of grippers 4 are in a single row in the width direction W of the bags (see FIG. 3).

The chuck-moving mechanism 3 of the bag unloading apparatus includes a pivot arm 8 that pivots back and forth through a predetermined angular range (set to be 45° in the shown structure) in the horizontal plane, a driving mechanism 9 for the pivot arm 8, a chuck-supporting frame 11 rotatably mounted to the free end of the pivot arm 8 in the horizontal plane, a chuck-supporting frame rotation mechanism 12 that rotates the chuck-supporting frame 11 back and forth with respect to the pivot arm 8 through a predetermined angular range (set to be 135° in the shown structure), and a chuck rotation mechanism 13 that rotates the chucks 1 back and forth with respect to the chuck-supporting frame 11 through a predetermined angular range (set to)90°.

The chuck-supporting frame 11 has a pivot shaft 14 perpendicularly secured fixedly at its center position in the length direction, and this pivot shaft 14 is rotatably supported on the free end of the pivot arm 8.

Each of the chucks 1 is comprised of a pair of downwardly opening and closing jaws 1a and 1b and installed underneath chuck-actuating air cylinders 15, and they are opened and closed under the action of the air cylinders 15 (in FIG. 2, the solid lines indicate the open state and the dotted lines indicate the closed state). When closed, the chucks grasp from above the sealed mouth of the product bag 2 practically along the entire width of the bag. A pivot shaft 16 is perpendicularly fixedly secured to the upper end of each of the air cylinders 15, and the pivot shafts 16 are rotatably fitted to the both ends of the chuck-supporting frame 11. As a result, the chucks 1 are rotatable about the pivot shafts 16 located in the center thereof in the width direction so that the chucks 1 are rotated in the horizontal plane with respect to the chuck-supporting frame 11. The chucks 1 are installed at equidistant positions on both sides of the pivot shaft 14 of the chuck-supporting frame 11 (the two pivot shafts 16 are provided at equal distant points from the pivot shaft 14).

The driving mechanism 9 of the pivot arm 8 includes a stand 18, which is set upright on a mount 17, a hollow shaft 19 rotatably installed in the stand 18, and a drive source (not shown). The base portion of the pivot arm 8 is fixedly secured to the hollow shaft 19. The center of the hollow shaft 19 serves as the axis of rotation for the pivotal motion of the pivot arm 8.

The chuck-supporting frame rotation mechanism 12 includes a vertical shaft 21 supported in the hollow shaft 19 (rotatable with respect to the hollow shaft 19) and fixedly secured to the bottom portion of the mount, a first pulley (timing pulley) 22 fixedly secured to the upper end of the vertical shaft 21, the pivot shaft 14 described above, a second pulley (timing pulley) 23 fixedly secured to the upper end of the pivot shaft 14, and a timing belt 24 provided over the first and second pulleys 22 and 23.

When the pivot arm 8 pivots by the action of the driving mechanism 9, the driving force of the drive source is transmitted to the chuck-supporting frame rotation mechanism 12, thereby rotating the chuck-supporting frame 11 with respect to the pivot arm 8 via the pivot shaft 14. The direction of rotation of the chuck-supporting frame 11 is opposite to the direction of the pivotal motion of the pivot arm 8, and the pulley ratio of the first and second pulleys 22 and 23 is set so that, in response to 45-degree reciprocating pivotal motion of the pivot arm 8, the chuck-supporting frame 11 correspondingly makes a 135-degree reciprocating rotary motion. Accordingly, in terms of absolute angles, the chuck-supporting frame 11 changes its orientation by 90° while the pivot arm 8 rotates through 45°.

The chuck rotation mechanism 13 includes a first gear 25 that is fixedly secured to the free end of the pivot arm 8 concentrically (or coaxially) with the pivot shaft 14 of the chuck-supporting frame 11, the pivot shafts 16 of the chucks 1 described above, a pair of second gears 26 which are respectively fixedly secured to the pivot shafts 16, and a pair of third gears 27, which are respectively rotatably mounted to the chuck-supporting frame 11 and are interposed between the first gear 25 and second gears 26 in mesh with these first and second gears 25 and 26. When viewed from above, both second gears 26 are shaped like one-quarter circular arcs, and their centers coincide with the axes of rotation of the pivot shafts 16.

When the pivot arm 8 pivots by the action of the driving mechanism 9, the driving force of the drive source is transmitted to the chuck-supporting frame rotation mechanism 12 and then to the two chucks 1 via the chuck rotation mechanism 13, thereby causing the chucks 1 to rotate with respect to the chuck-supporting frame 11. The reciprocating rotary motion of the chuck-supporting frame 11 and chucks 1 is set so as to be in synchronism with the reciprocating pivotal motion of the pivot arm 8. The direction of rotation of the chucks 1 is opposite to that of the chuck-supporting frame 11. The gear ratio of the first gear 25 and second gears 26 is set so that, for a 135-degree reciprocating rotary motion of the chuck-supporting frame 11, the chucks 1 correspondingly make a 90-degree reciprocating rotary motion.

In the structure described above, as seen from FIGS. 1 through 3, at the moment when the pairs of grippers 4 of the intermittently-conveying bag packaging machine grip the product bags 2 and make a stop, the pivot arm 8 is at the starting point of its pivotal motion, while the chuck-supporting frame 11 and chucks 1 are at the starting point of their rotary motion. In other words, the chuck-supporting frame 11 is positioned directly above the product bags 2, which are arranged in a single row in the width direction of the bags as seen from FIG. 3, and is in parallel to the row of the product bags 2. In addition, the chucks 1 are directly above the product bags 2 in a single row in the width direction W of the bags 2 (in other words, chucks 1 are along the width direction of the grasping surfaces of the chucks 1). The position of the chucks 1 at this time is the receiving position.

Before gripping the product bags 2, the chucks are in an open state as shown in FIG. 1 (and by the dotted line in FIG. 2). After that, the air cylinders 15 are actuated to close the chucks 1 so that the chucks 1 grip the mouths of the product bags 2 as shown in FIGS. 2 and 3. Subsequently, the pairs of grippers 4 open and release the product bags 2 that are held by the chucks 1.

Figure 4:
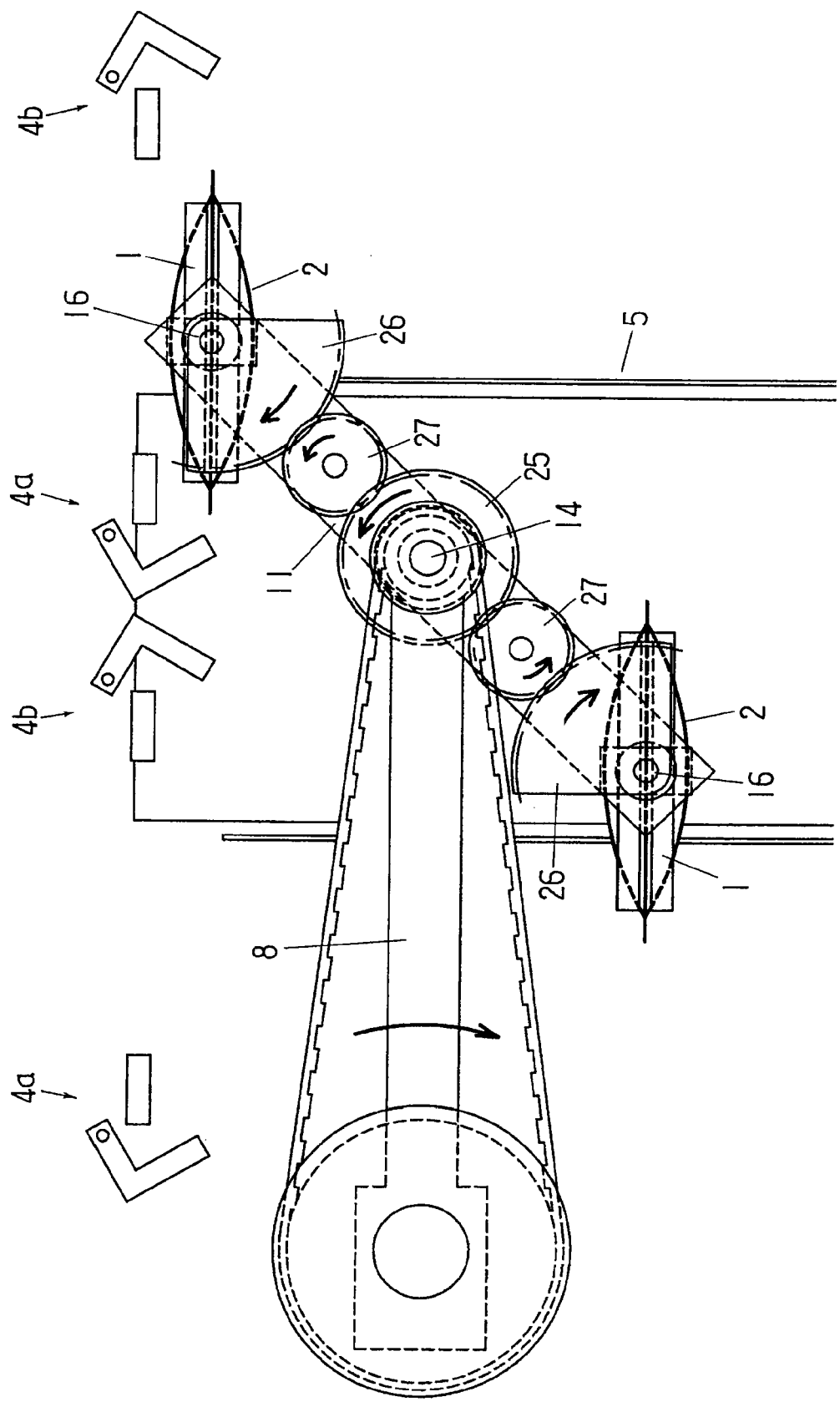
FIG. 4 is a plan view of the duplex-type product bag unloading apparatus with the chucks in transit from the receiving position to the discharging position.

As the pivot arm 8 begins to pivot (rotate clockwise in FIG. 3), the chuck-supporting frame 11 and chucks 1 begin to rotate simultaneously. FIG. 4 shows the positions of the pivot arm 8, chuck-supporting frame 11, and chucks 1, when the pivot arm 8 is in the process of its pivotal motion (pivoting angle being 45°/2). In FIG. 4, the direction of pivotal motion of the pivot arm 8, the direction of rotation of the chuck-supporting frame 11, the direction of rotation of the chucks 1 (and second gears 26), and the direction of rotation of the third gears 27 are indicated by arrows. It should be noted that while the first gear 25 pivots with the pivot arm 8, the first gear 25 does not rotate about its axis (the first gear 25 is fixedly secured to the pivot arm 8).

As described above, while the pivot arm 8 pivots, the chuck-supporting frame 11 rotates through an absolute angle of 90°. At the same time, the chucks 1 rotate in the opposite direction through a relative angle of 90° with respect to the chuck-supporting frame 11. Consequently, the chucks 1 do not rotate through an absolute angle, and the orientation of the chucks 1 and product bags 2 does not change while in transit from the receiving position to the discharging position. In other words, the chucks 1 and product bags 2 make a translational motion.

Figure 5:
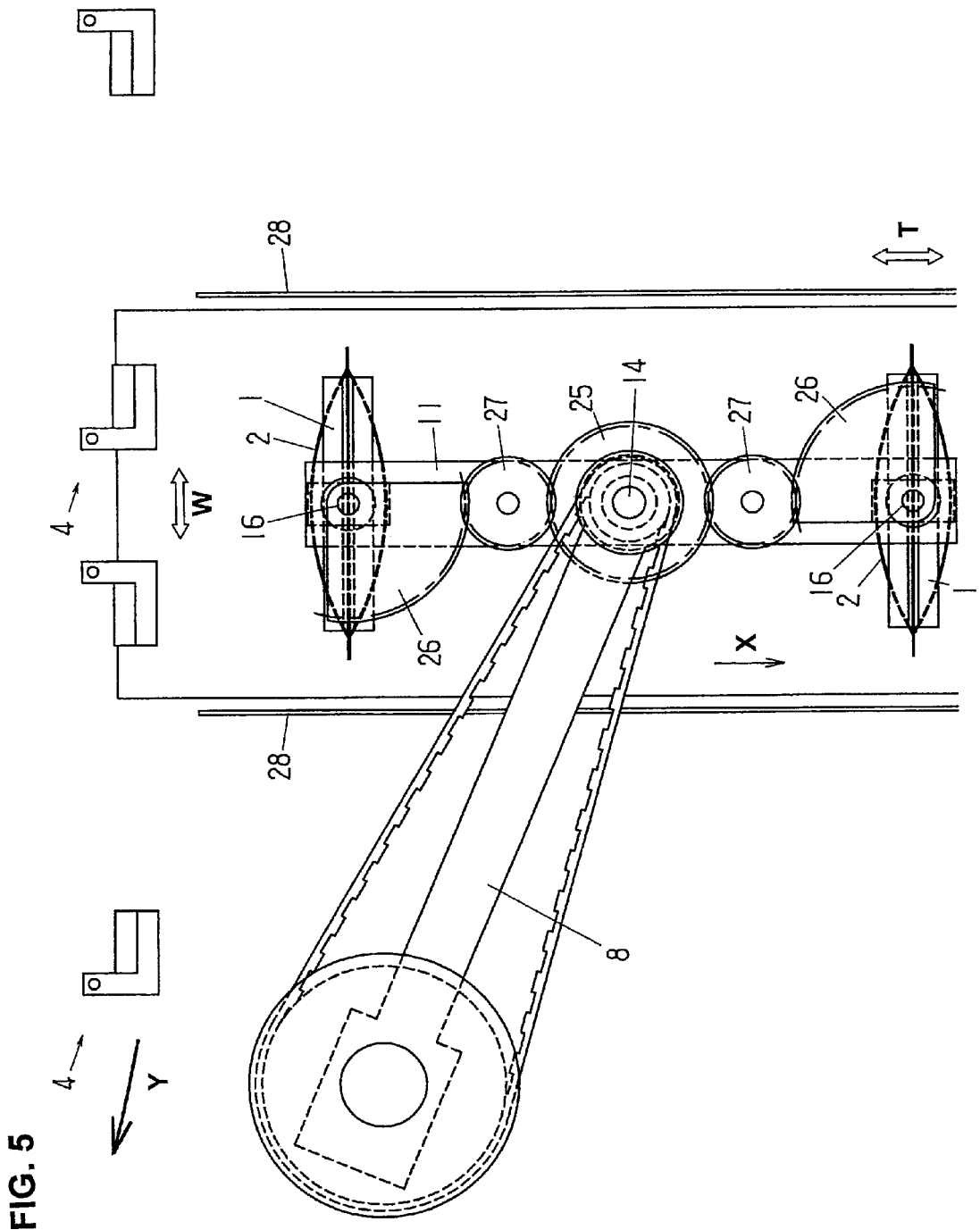
FIG. 5 is a plan view of the duplex-type product bag unloading apparatus of the present invention with the chucks in the discharging position.

When the pivot arm 8 reaches the end point of pivotal motion (the position it arrives at after pivoting through)45°, the chuck-supporting frame 11 and chucks 1 reach the end point of rotary motion. At this point, as shown in FIG. 5, the chuck-supporting frame 11 has rotated through 90° from the starting position of the rotary motion and becomes parallel to the direction of conveyance of the carry-out conveyor 5 (the direction of the arrow X). As the chucks 1 and product bags 2 rotate through 90° from the starting position of rotary motion with respect to the chuck-supporting frame 11, their width direction becomes perpendicular to the length direction of the chuck-supporting frame 11, and they become to be arranged in a single row along the thickness direction T of the product bags 2 (in other words, they are arranged in a single row in a direction perpendicular to the grasping surfaces of the chucks 1). The position of the chucks 1 at the end point of rotary motion is the discharging position.

At this point, the pairs of grippers 4 are closed (they can remain open) and are about to start moving towards the next stopping position (in the direction of the arrow Y).

Subsequently, the chucks 1 are opened in the discharging position, and the product bags 2 are dropped onto the carry-out conveyor 5 (see FIG. 6). After falling, the length direction of the bags is oriented in the direction of conveyance of the conveyor, and the product bags 2 dropped onto the carry-out conveyor 5 are carried out in a single-row alignment. The two chucks 1 do not have to be opened simultaneously, and it can be designed so that, for example, the chuck located in front in the direction of conveyance is opened first. The reference numeral 28 in FIG. 1 and in other figures refers to side guide plates of the carry-out conveyor 5.

After the chucks 1 have opened and released the product bags 2, the pivot arm 8 pivots back towards the starting point of pivotal motion (the position in FIG. 3) and, at the same time, the chuck-supporting frame 11 and the chucks 1 also are rotated, toward the starting point of rotary motion, back in a direction opposite to that of the forward motion.

In the present invention, the orientation (lengthwise orientation) of the product bags 2 dropped onto the carry-out conveyor 5 can be more reliably aligned along the direction of conveyance of the carry-out conveyor 5 when the carry-out conveyor 5 are provided so that it is movable between a lowered position, in which the conveying surface is lower than the bottom ends of the product bags 2, and a raised position, in which the conveying surface are raised higher than the bottom of the product bags 2, so that the carry-out conveyor 5 can be moved up and down at appropriate timing. In this structure, with the carry-out conveyor 5 being in the lowered position, when the chucks 1 arrive at the discharging position and the carry-out conveyor 5 is raised, the bottom ends of the product bags 2 grasped at the mouths by the chucks are brought into contact with the conveyor belt 29, and the conveyor 5 receives the bottom ends of the product bags 2. Then, by opening the chucks 1, the product bags 2 fall onto the conveyor belt 29 such that their lengthwise orientation is aligned along the direction of conveyance of the conveyor belt 29, making it possible to avoid disturbing the orientation and positions of the product bags 2 at the time of release of the bags from the chucks 1.

Figure 6:
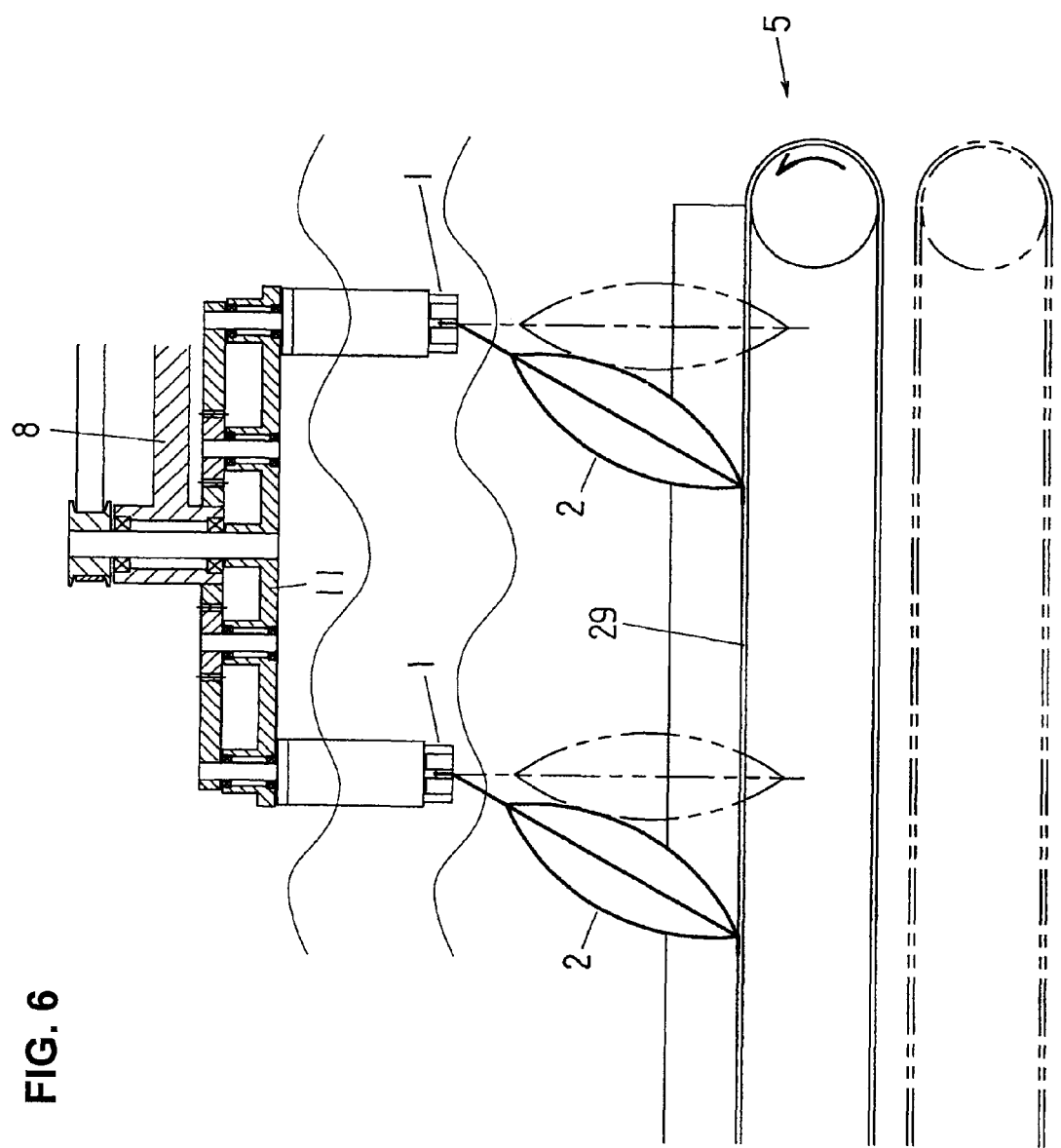
FIG. 6 is an explanatory drawing illustrating the movement of product bags when the product bags are discharged onto a carry-out conveyor that is raised (in solid lines) and lowered (broken lines)
Figure 7:
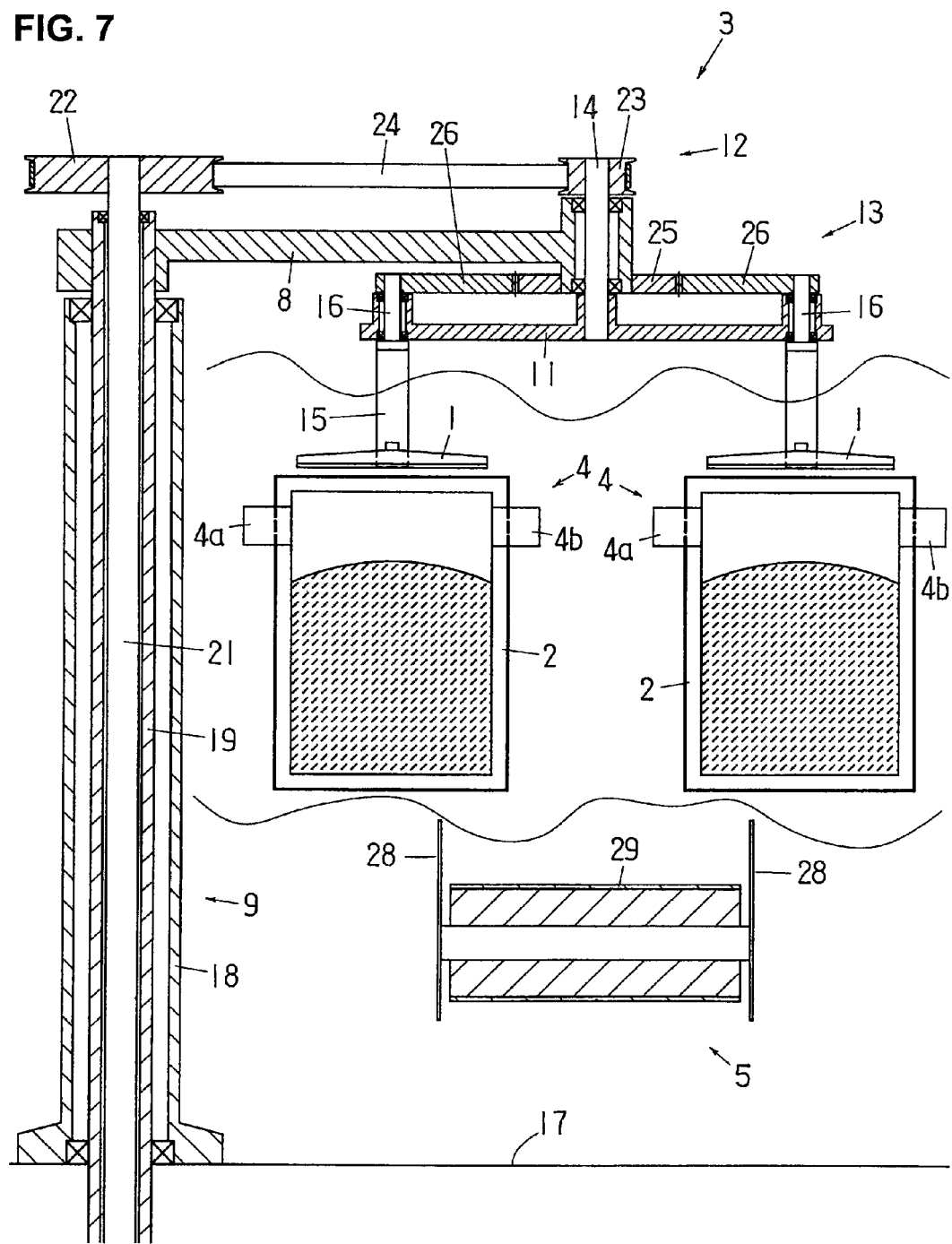
FIG. 7 is a partial cross-sectional front view of another duplex-type product bag unloading apparatus according to the present invention with the chucks in the receiving position (with the chucks open)
Figure 8:
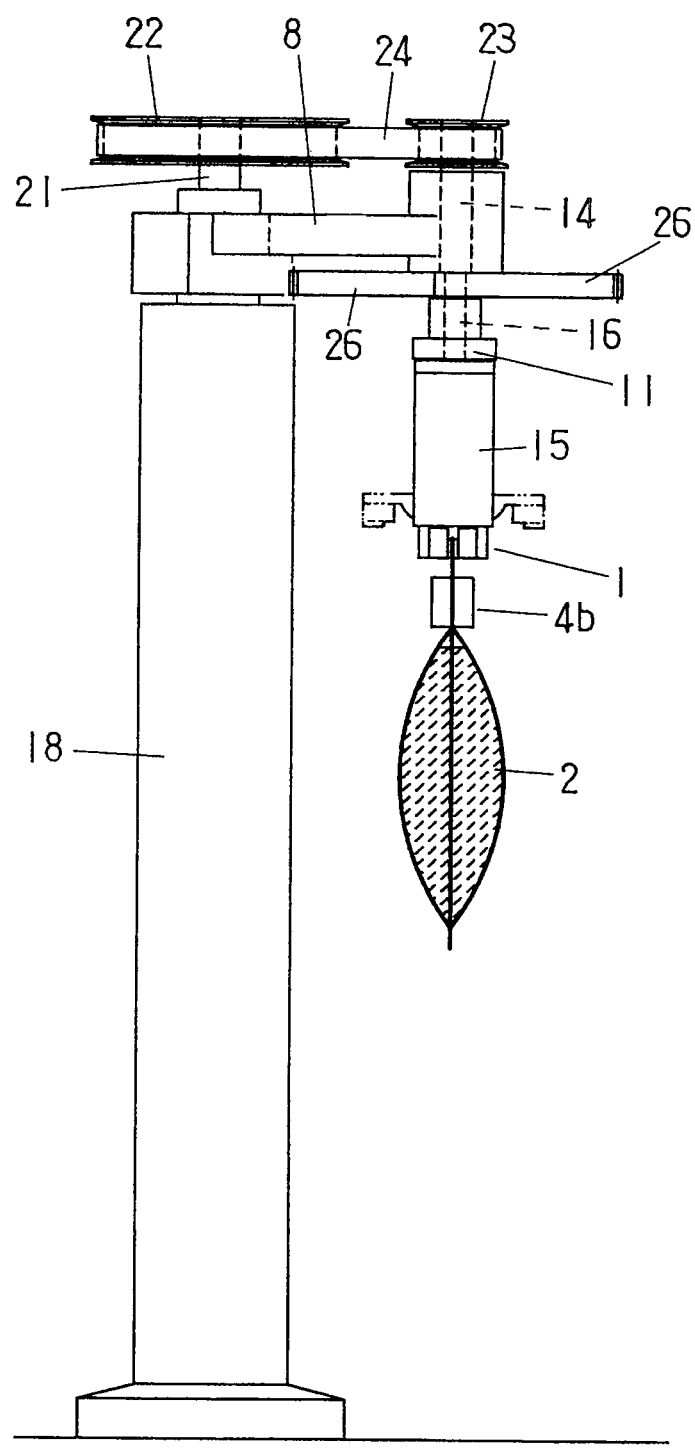
FIG. 8 is a side view thereof (with the chucks closed)

In this case, as shown in FIG. 6, when the carry-out conveyor 5 are actuated in advance, it is possible to make the product bags 2 fall more consistently in the same direction (with the bottom side of the bags facing in the direction of conveyance). In FIG. 6, when the carry-out conveyor 5 is in a lowered position (indicated by the dotted lines), in which the conveying surface is lower than the bottom ends of the product bags 2, the chucks 1 arrive at the discharging position; and when the carry-out conveyor 5 is raised to a raised position, in which the conveying surface of the carry-out conveyor 5 is located higher than the bottom ends of the product bags 2, the bottom ends of the product bags 2 (indicated by the dotted lines) gripped by the chucks 1, upon coming into contact with the traveling conveyor belt 29, are pulled in the direction of conveyance and tilted as shown by the solid lines; and when the chucks 1 are opened at this moment, the product bags 2 fall onto the traveling conveyor belt 29 with the bottom side of the bags facing in the direction of conveyance.

In the description above, since the product bag unloading apparatus is provided outside of the circular travel path of the pairs of grippers 4, the product bags 2 fall onto the conveyor belt 29 in such a manner that the side that was oriented outwardly from the travel path when they were gripped by the pairs of grippers 4 become to face upward.

As far as the timing of the raising and lowering of the carry-out conveyor 5 is concerned, basically, the conveyor can be raised after the chucks 1 have arrived at the discharging position and lowered prior to starting movement from the receiving position. However, in order to avoid interference with the product bags 2 gripped by the pairs of grippers 4 when the conveying path of the pairs of grippers 4 of the intermittently-conveying bag packaging machine overlaps with the carry-out conveyor 5 in plan view, it is preferable that the conveyor be lowered at an earlier point in time before the product bags have arrived at the receiving position.

Instead of raising and lowering the carry-out conveyor 5 as described above, the chucks 1 can be designed so as to be raised and lowered.

As an additional benefit, the rotary motion of the pivot arm 8 in the above-described duplex-type product bag unloading apparatus is to keep the chucks 1 and grasped product bags 2 away from the bag packaging machine and, in particular, the pairs of grippers 4 thereof, thereby preventing interference of the chucks 1 and bags 2 with the grippers 4.

In addition, the 135-degree turn of the chuck-supporting frame 11 with respect to the pivot arm 8 ensures a large absolute angle of rotation of the chuck-supporting frame 11 even when the pivoting angle of the pivot arm 8 is small. Although the pivoting angle of the pivot arm 8 in the above-described example is 45°, the absolute angle of rotation (change in orientation) of the chuck-supporting frame 11 is 90°, as a result of which the product bags 2 can be discharged onto the carry-out conveyor 5, whose direction of conveyance is oriented in the radial direction of the circular travel path of the pairs of grippers 4. Accordingly, it is possible that the chucks 1 take less time to travel from the receiving position to the discharging position and make the travel distance shorter, and the deflection and shifting of the product bags 2 can be minimized.

In addition, the rotation of the chucks 1 with respect to the chuck-supporting frame 11 makes the product bags 2 be arranged, in the discharging position, in a single row in the direction of conveyance of the carry-out conveyor 5 and aligns the length direction of the bags along the direction of conveyance of the carry-out conveyor 5.

Second Embodiment

The second embodiment of the duplex-type product bag unloading apparatus of the present invention will be described below with reference to FIGS. 7 through 11. In FIGS. 7 through 11, the elements substantially the same as those in FIGS. 1 through 6 are given the same reference numerals.

The product bag unloading apparatus of the second embodiment is structurally different from the product bag unloading apparatus of the first embodiment only in that no third gears 27 are provided, and the first gear 25 is directly in mesh with the second gears 26. In addition, another difference is that while the chucks 1 rotate through a relative angle of 90° with respect to the chuck-supporting frame 11, the direction of their rotation coincides with the direction of the chuck-supporting frame 11 due to the structural difference from the first embodiment.

The following description of the product bag unloading apparatus of FIGS. 7 through 11 will focus mainly on the structure related to the above-described differences.

In this product bag unloading apparatus, the pivot arm 8 pivots back and forth through an angular range of 45°. As a result, the chuck-supporting frame 11 rotates back and forth through an angular range of 135° in the opposite direction with respect to the pivot arm 8. Accordingly, the chuck-supporting frame 11 changes its orientation by 90° while the pivot arm 8 rotates through 45°. In addition, as the pivot arm 8 pivots back and forth through the angular range of 45°, the chucks 1 rotate back and forth through 90° with respect to the chuck-supporting frame 11. These features are the same as those of the product bag unloading apparatus of FIGS. 1 through 6.

The chuck rotation mechanism 13 of the second embodiment, however, includes a first gear 25 which is secured to the free end of the pivot arm 8 in concentric with the pivot shaft 14 of the chuck-supporting frame 11, pivot shafts 16 of the chucks 1, and a pair of second gears 26 which are fixedly secured to the pivot shafts 16 and are in mesh with the first gear 25 on both sides thereof. Each of the second gears 26 is, when viewed from above, shaped like a one-quarter circular arc.

The driving force of the pivot arm 8 is transmitted to the two chucks 1 via the chuck-supporting frame rotation mechanism 12 and the chuck rotation mechanism 13 and, just like in the product bag unloading apparatus shown in FIG. 1-FIG. 6, the chucks 1 rotate through 90° with respect to the chuck-supporting frame 11. However, since in the structure of FIGS. 7 through 11 the chuck rotation mechanism 13 does not have the third gears 27, the direction of rotation of the chucks 1 differs from that of the product bag unloading apparatus shown in FIG. 1-FIG. 6 and coincides with that of the chuck-supporting frame 11.

The reciprocating pivotal motion of the pivot arm 8 and the reciprocating rotary motion of the chuck-supporting frame 11 and chucks 1 in this product bag unloading apparatus of the second embodiment will be described specifically with reference to FIGS. 9 through 11.

Figure 9:
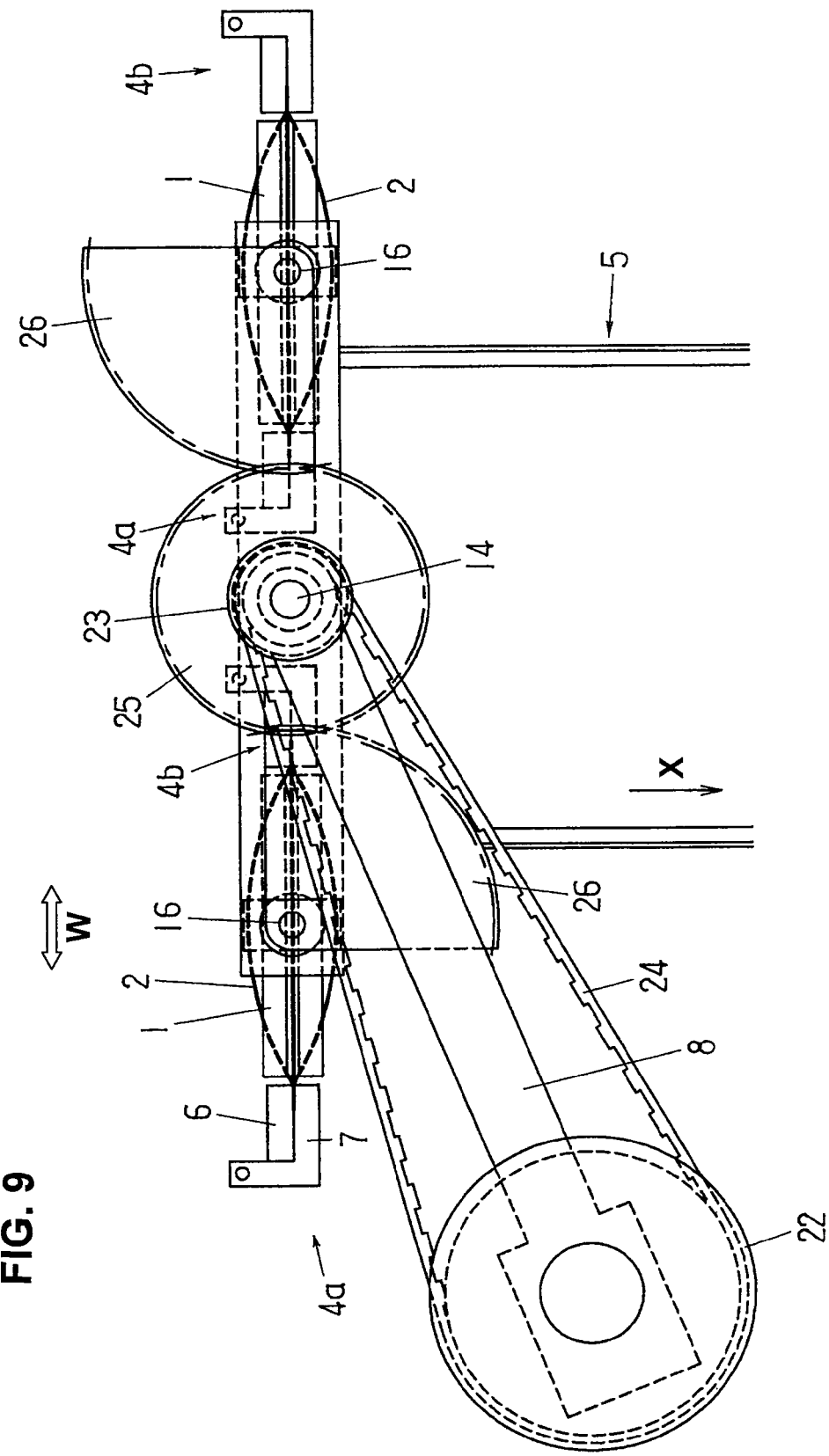
FIG. 9 is a plan view thereof (with the chucks closed)
Figure 10:
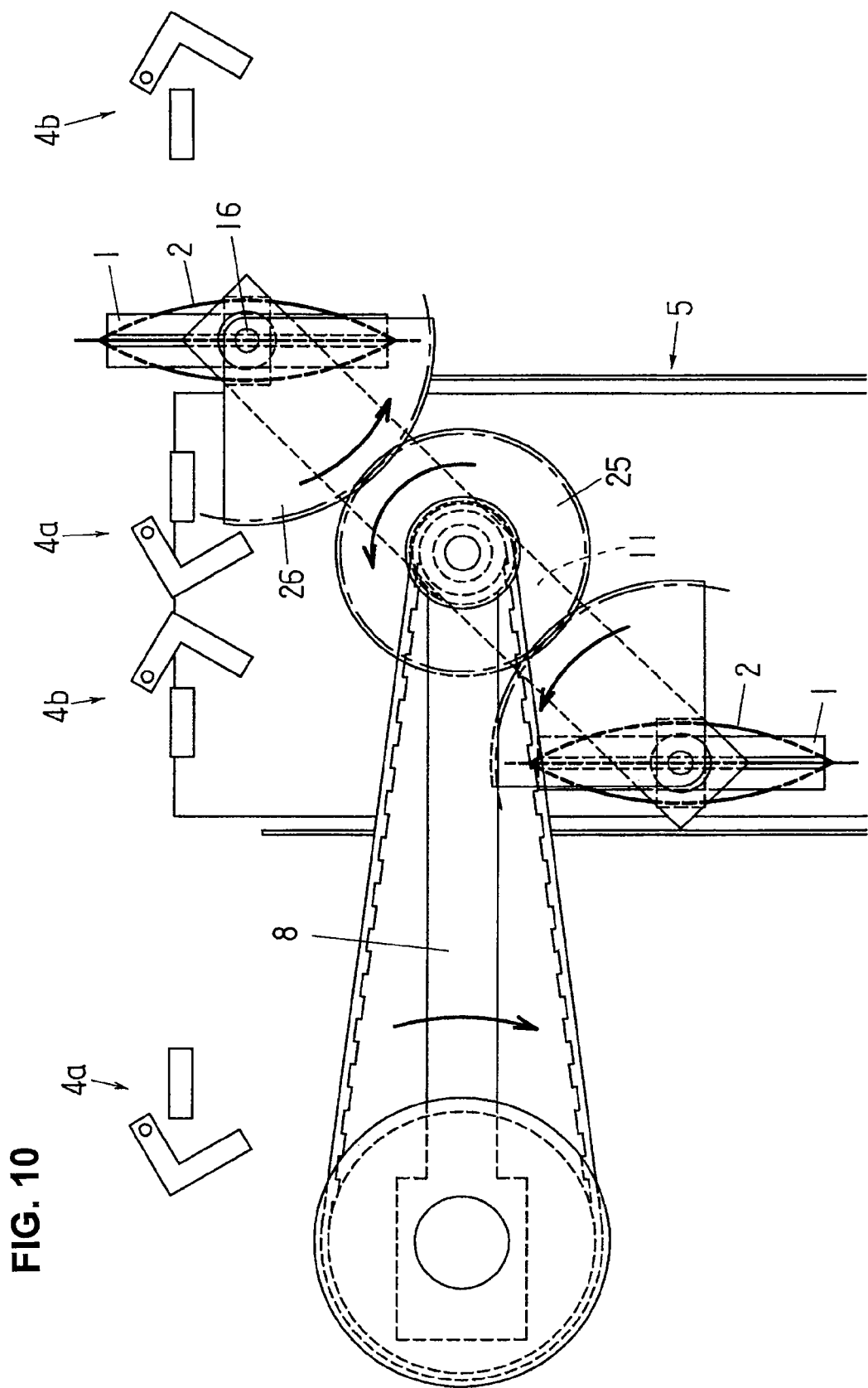
FIG. 10 is a plan view of the other duplex-type product bag unloading apparatus of the present invention with the chucks in transit from the receiving position to the discharging position.

As shown in FIG. 9, at the moment when the pairs of grippers 4 of the intermittently-conveying bag packaging machine grip the product bags 2 and make a stop, the pivot arm 8 is at the starting point of its pivotal motion, while the chuck-supporting frame 11 and chucks 1 are at the starting point of their rotary motion. In other words, the chuck-supporting frame 11 is positioned directly above the product bags 2, which are arranged in a single row in the width direction of the bags as seen from FIG. 9, and is in parallel to the row of the product bags 2. In addition, the chucks 1 are directly above the product bags 2 arranged in a single row in the width direction W of the bags 2. The position of the chucks 1 at this time is the receiving position. These features are identical to those of the product bag unloading apparatus of FIG. 1-FIG. 6.

As the pivot arm 8 begins to pivot (rotate clockwise in FIG. 9), the chuck-supporting frame 11 and chucks 1 begin to rotate simultaneously. FIG. 10 shows the position of the pivot arm 8, chuck-supporting frame 11, and chucks 1 when the pivot arm 8 is in the process of the pivotal motion (pivoting angle being 45°/2). In FIG. 10, the direction of pivotal motion of the pivot arm 8, the direction of rotation of the chuck-supporting frame 11, and the direction of rotation of the chucks 1 (and second gears 26) are indicated by arrows. It should be noted that while the first gear 25 pivots with the pivot arm 8, the first gear 25 does not rotate about its axis (the first gear 25 is fixedly secured to the pivot arm 8).

As described above, while the pivot arm 8 pivots, the chuck-supporting frame 11 rotates through an absolute angle of 90°. At the same time, the chucks 1 rotate in the same direction through a relative angle of 90° with respect to the chuck-supporting frame 11. Consequently, the chucks 1 rotate through an absolute angle of 180°, and the orientation of the chucks 1 and product bags 2 changes 180° while in transit from the receiving position to the discharging position. These movements are different from those in the product bag unloading apparatus illustrated in FIGS. 1 through 6.

When the pivot arm 8 reaches the end point of pivotal motion (the position it arrives at after pivoting through)45°, the chuck-supporting frame 11 and chucks 1 reach the end point of the rotary motion. At this point, as shown in FIG. 11, the chuck-supporting frame 11 rotates through 90° from the starting position of the rotary motion and becomes parallel to the direction of conveyance of the carry-out conveyor 5 (the direction of the arrow X). As the chucks 1 and product bags 2 rotate through 90° from the starting position of the rotary motion with respect to the chuck-supporting frame 11, their width direction becomes perpendicular to the length direction of the chuck-supporting frame 11, and they become to be arranged in a single row along the thickness direction of the product bags 2.

However, since the orientation of the product bags 2 changes 180° while the chucks 1 transition from the receiving position to the discharging position, if the carry-out conveyor 5, while in operation, is raised in the discharging position (see FIG. 6), the bottom ends of the product bags 2 grasped by the chucks 1 are pulled in the direction of conveyance by the traveling conveyor belt 29, and by opening the chucks 1, the product bags 2 fall onto the traveling conveyor belt 29 in such a manner that the surface that was oriented outward of the travel path when they were gripped by the pairs of grippers 4 faces downward (thus being the reverse from the product bag unloading apparatus of FIG. 1-FIG. 6).

In the first embodiment of the bag unloading apparatus shown in FIGS. 1 through 6, the width orientation of the chucks 1 and product bags 2 is kept constant (tangential to the travel path of the pairs of grippers 4) while the chucks 1 reciprocated between the receiving position and discharging position. However, this feature is not essential in the present invention. In other words, the width orientation of the chucks 1 and product bags 2 does not have to be kept constant as shown in the bag unloading apparatus of the second embodiment (FIGS. 7 through 11) during the process of moving between the receiving position and the discharging position. First embodiment is preferable in that the product bags 2 are prevented from shifting.

Other Embodiments

It should be noted that the structure and operation of the duplex-type product bag unloading apparatus of the present invention is not limited to those described above. Various modifications in the following paragraphs can be employed as well in the present invention.

(1) In the above-described duplex-type product bag unloading apparatuses, the drive source of the rotary motion of the chuck-supporting frame 11 and chucks 1 is the same as the drive source of the pivot arm 8. Nonetheless, it is possible to design so that the chuck-supporting frame 11 and/or the chucks 1 are rotated using a separate drive source. For example, it can be contemplated to eliminate the vertical shaft 21, first and second pulleys 23 and 24 and timing belt 24 of the chuck-supporting frame rotation mechanism 12 and provide a separate drive source for rotating the pivot shaft 14 (with the chucks 1 to be rotated by the chuck rotation mechanism 13), and it can be also contemplated to eliminate the first gear 25 and second gears 26 of the chuck rotation mechanism 13 and provide a separate drive source for rotating the pivot shafts 16 (with the chuck-supporting frame 11 to be rotated by the chuck-supporting frame rotation mechanism 12 or, as described above, by a separately provided drive source). If the drive source used for rotating the chuck-supporting frame 11 and/or the chucks 1 is not the same as (or not common to) the drive source of the pivot arm 8, then the rotation of the chuck-supporting frame 11 and/or the chucks 1 does not necessarily have to be synchronized with the pivotal motion of the pivot arm 8.

(2) In the above-described duplex-type product bag unloading apparatuses, the chuck-supporting frame 11 is rotatably mounted to the pivot arm 8. Nonetheless, it is possible to design so that the chuck-supporting frame 11 is fixedly attached to the pivot arm 8. Although in such a case the construction of the apparatus is simplified, the pivoting angle of the pivot arm 8 and the angular variation (absolute angle) of the orientation of the chuck-supporting frame 11 associated with the pivotal motion of the pivot arm 8 coincide. For this reason, if the direction of conveyance of the carry-out conveyor 5 is the same as that in the described embodiments, the pivoting angle of the pivot arm 8 needs to be set greater in comparison with the above-described embodiments. Therefore, the smaller the angular difference (90° in the above-described embodiments) between the direction of conveyance of the carry-out conveyor 5 in the receiving position and the circular travel path of the pairs of grippers 4, the more advantageous this construction becomes.

(3) In the above-described duplex-type product bag unloading apparatuses, the direction of conveyance of the carry-out conveyor 5 in the receiving position is set at an angle of 90° with respect to the travel path of the pairs of grippers 4. This angle, nonetheless, can be set in an arbitrary manner. No matter what angle it is set to, however, when the chucks 1 reach the discharging position, the chuck-supporting frame 11 needs to become parallel to the direction of conveyance of the carry-out conveyor 5 and the chucks 1 need to be in a single row along the thickness direction of the product bags 2 (which is the same as the direction of conveyance), with their width direction being perpendicular to the length direction of the chuck-supporting frame 11.

(4) In the above-described duplex-type product bag unloading apparatuses, the direction of rotation of the chuck-supporting frame 11 is set to be a direction that is opposite to the pivoting direction of the pivot arm 8. Nonetheless, the direction of rotation of the chuck-supporting frame 11 can be set to be the same direction as the pivoting direction of the pivot arm 8. In this case, if the pivoting angle of the pivot arm 8 is 45° as in the above-described embodiments, then the angle of rotation of the chuck-supporting frame 11 with respect to the pivot arm 8 can be set to be 45°.

FIGS. 12(*a*) and 12(*b*) schematically illustrate part of a duplex-type product bag unloading apparatus (see FIGS. 1 through 6) in which the width orientation of the chucks 1 and product bags 2 is kept constant while the chucks 1 reciprocate between the receiving position and discharging position, and they further illustrate positions of the pivot arm 8, product bags 2, chuck-supporting frame 11 and pairs of grippers 4 when the direction of rotation of the chuck-supporting frame 11 is either opposite to the pivoting direction of the pivot arm 8 (FIG. 12(*a*)) or the same (FIG. 12(*b*)). In FIGS. 12(*a*) and 12(*b*), the solid line represents the pivot arm 8 in the starting position of pivotal motion (when the chucks are in the receiving position), and the dotted line represents it in the process of pivoting (the pivoting angle of the pivot arm 8 being 45°/2).

In FIGS. 12(*a*) and 12(*b*), the solid and dotted lines show the trajectories 31 and 32 of the ends of the product bags 2 that may easily interfere with opened pairs of grippers 4. In the case of FIG. 12(*a*), the travel distance L1 of the product bag 2 in the width direction is smaller than the travel distance L2 in the case of FIG. 12(*b*); and in both cases the travel distance in the bag thickness direction of the product bag 2 is nearly the same. For this reason, the angle of tilt of the trajectory 31 with respect to the plane 33 (the angle of deviation from the plane 33 through 33), along which the pairs of grippers 4 are aligned, is larger than the angle of tilt of the trajectory 32 (the angle of deviation from the plane 33 through 33) and, as a result, the advantage is that interference with the pairs of grippers 4 is easier to avoid.

(5) Although the above-described duplex-type product bag unloading apparatuses are used with a duplex type intermittently-conveying bag packaging machine, they can also be used with a duplex type intermittently conveying vacuum packaging machine (see Japanese Utility Model Registration No. 3116531).

(6) Furthermore, although the product bags discharged from the above-described duplex-type product bag unloading apparatuses are discharged onto a conveyor belt (carry-out conveyor 5), they can be discharged onto a bucket conveyor described in, for instance, Japanese Patent No. 3984740.

The invention claimed is:

1. A duplex-type product bag unloading apparatus that receives two filled and sealed product bags, which are gripped by separate pairs of grippers respectively on left and right edges thereof, suspended mouth-side-up at equal heights, and arranged in a single row in a width direction thereof at a predetermined distance apart from each other, from said pairs of grippers and discharges the bags onto a carry-out conveyor; wherein said unloading apparatus comprises:

two downwardly opening and closing chucks for grasping, from above, areas around mouths of the product bags gripped by said pairs of grippers, and a chuck-moving mechanism for reciprocating said two chucks between a product bag-receiving position and a discharging position which is remote from the receiving position; and said two chucks being rotatably supported in a horizontal plane in a chuck-supporting frame that is a part of the chuck-moving mechanism and being rotated ninety degrees, with respect to the chuck-supporting frame, by the chuck-moving mechanism while the chucks are being moved between the receiving position and the discharging position, such that in the receiving position, said chucks are arranged in a single row along a bag width direction of the grasped product bags, said bag width direction being a width direction of grasping surfaces of the chucks, and in the discharging position, said chucks are arranged in a single row along a thickness direction of the grasped product bags, said thickness direction being a direction that is perpendicular to the grasping surfaces of the chucks.

2. The duplex-type product bag unloading apparatus according to claim 1, wherein an orientation of the bag width direction of the product bags grasped by said chucks is kept substantially constant while said chucks reciprocate between the receiving position and the discharging position.

3. The duplex-type product bag unloading apparatus according to claim 2, wherein said chuck-moving mechanism comprises:

a pivot arm which is coupled to a drive source and pivots back and forth through a predetermined angular range in a horizontal plane, and said chuck-supporting frame which is attached to a free end of said pivot arm; and while said pivot arm pivots back and forth, said two chucks rotate back and forth through a 90-degree range with respect to said chuck-supporting frame.

4. The duplex-type product bag unloading apparatus according to claim 1, wherein:

said chuck-moving mechanism comprises a pivot arm which is coupled to a drive source and pivots back and forth through a predetermined angular range in a horizontal plane, and said chuck-supporting frame, which is journaled on a free end of said pivot arm for making reciprocating rotary motion in the horizontal plane; and wherein said two chucks are rotatably supported in the horizontal plane on opposite sides of a pivot shaft of said chuck-supporting frame, and while the pivot arm pivots back and forth, the chuck-supporting frame rotates back and forth through a predetermined angular range with respect to said pivot arm, and said two chucks rotate back and forth through a 90-degree range with respect to said chuck-supporting frame.

5. The duplex-type product bag unloading apparatus according to claim 4, wherein the orientation of the bag width direction of the product bags grasped by said chucks is kept substantially constant while said chucks reciprocate between the receiving position and the discharging position.

6. The duplex-type product bag unloading apparatus according to claim 5, wherein a reciprocating rotary motion of said chuck-supporting frame and said two chucks is set so as to be in synchronism with the reciprocating pivotal motion of said pivot arm.

7. The duplex-type product bag unloading apparatus according to claim 4, wherein a reciprocating rotary motion of said chuck-supporting frame and said two chucks is set so as to be in synchronism with the reciprocating pivotal motion of said pivot arm.

8. The duplex-type product bag unloading apparatus according to claim 7, wherein a direction of the rotation of the reciprocating rotary motion of said chuck-supporting frame is set so as to be oriented in a direction opposite to a direction of rotation of the reciprocating pivotal motion of said pivot arm.

9. The duplex-type product bag unloading apparatus according to claim 6, wherein a direction of the rotation of the reciprocating rotary motion of said chuck-supporting frame is set so as to be oriented in a direction opposite to a direction of rotation of the reciprocating pivotal motion of said pivot arm.

10. The duplex-type product bag unloading apparatus according to any one of claims 7 through 9, wherein
- a drive source for rotating said chuck-supporting frame and said two chucks back and forth is the same as the drive source for pivoting said pivot arm back and forth, and
- said chuck-moving mechanism includes:
  - a chuck-supporting frame rotation mechanism which transmits a driving force of the drive source to said chuck-supporting frame, and
  - a chuck rotation mechanism which further transmits the driving force transmitted by said chuck-supporting frame rotation mechanism to said two chucks.

11. The duplex-type product bag unloading apparatus according to claim 10, wherein
- said chuck-supporting frame rotation mechanism comprises:
  - a first pulley provided at a turning center of said pivot arm,
  - a second pulley provided on said pivot shaft of said chuck-supporting frame, and
  - a belt provided over said first pulley and second pulley; and
- said chuck rotation mechanism comprises:
  - a first gear provided at the free end of the pivot arm and coaxial with said pivot shaft of said chuck-supporting frame,
  - a pair of second gears provided on pivot shafts of said two chucks, and
  - a pair of third gears which are rotatably mounted on said chuck-supporting frame in such a manner that said third gears are respectively interposed between said first gear and second gears while being in mesh with said first and second gears.

12. The duplex-type product bag unloading apparatus according to claim 1, wherein
- said chuck-moving mechanism comprises:
  - a pivot arm which is coupled to a drive source and pivots back and forth through a predetermined angular range in a horizontal plane, and
  - said chuck-supporting frame which is attached to a free end of said pivot arm;
- and
- while said pivot arm pivots back and forth, said two chucks rotate back and forth through a 90-degree range with respect to said chuck-supporting frame.

* * * * *